US007922720B2

(12) United States Patent
May et al.

(10) Patent No.: US 7,922,720 B2
(45) Date of Patent: Apr. 12, 2011

(54) ORTHOPAEDIC CUTTING INSTRUMENT AND METHOD

(75) Inventors: Justin J. May, Warsaw, IN (US); Charles D. Persons, Columbia City, IN (US); Robert D. Krebs, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 0 days.

(21) Appl. No.: 12/372,357

(22) Filed: Feb. 17, 2009

(65) Prior Publication Data

US 2009/0177202 A1 Jul. 9, 2009

Related U.S. Application Data (62) Division of application No. 11/095,232, filed on Mar. 31, 2005, now abandoned.

(51) Int. Cl.
*A61B 17/00* (2006.01)
(52) U.S. Cl. .............................. 606/80; 606/79; 606/86 R
(58) Field of Classification Search .................. 606/171, 606/176, 179, 180, 86 R, 79–89, 65–68; 81/1.2, 81/1.5
See application file for complete search history.

(56) References Cited

U.S. PATENT DOCUMENTS

| 1,251,133 A | 12/1917 | Thiemer |
| 1,414,110 A | 4/1922 | Bocchio |
| 2,402,353 A | 6/1946 | Trautmann |
| 2,525,669 A | 10/1950 | Hainault |
| 2,710,000 A | 6/1955 | Cromer et al. |
| 3,128,768 A | 4/1964 | Mikelis |
| 3,682,177 A | 8/1972 | Ames et al. |
| 4,111,208 A | 9/1978 | Leuenberger |
| 4,285,618 A | 8/1981 | Shanley |
| 4,445,509 A * | 5/1984 | Auth .............................. 606/159 |
| 4,541,423 A * | 9/1985 | Barber ............................ 606/80 |
| 4,594,033 A * | 6/1986 | Peetz et al. .................... 408/156 |
| 4,646,738 A | 3/1987 | Trott |
| 4,714,478 A | 12/1987 | Fischer |
| 4,777,942 A | 10/1988 | Frey |
| 4,856,503 A | 8/1989 | Shelhas |
| 4,990,134 A * | 2/1991 | Auth .............................. 604/22 |
| 5,080,588 A | 1/1992 | O'Brien |
| 5,112,338 A | 5/1992 | Anspach |
| 5,269,785 A | 12/1993 | Bonutti |
| 5,312,408 A | 5/1994 | Brown |
| 5,342,363 A | 8/1994 | Richelsoph |
| 5,403,320 A | 4/1995 | Luman |
| 5,439,005 A | 8/1995 | Vaughn |
| 5,488,761 A | 2/1996 | Leone |
| 5,527,316 A | 6/1996 | Stone et al. |
| 5,540,694 A | 7/1996 | Decarlo |

(Continued)

FOREIGN PATENT DOCUMENTS

EP 0496636 A1 7/1992

(Continued)

OTHER PUBLICATIONS

Restriction Requirement mailed Jul. 10, 2008 in parent U.S. Appl. No 11/095,232.

(Continued)

*Primary Examiner* — Eduardo C Robert
*Assistant Examiner* — Jan Christopher Merene
(74) *Attorney, Agent, or Firm* — Baker & Daniels LLP (57) ABSTRACT

An orthopaedic cutting instrument and associated methods are presented.

15 Claims, 4 Drawing Sheets

U.S. PATENT DOCUMENTS

| | | | |
|---|---|---|---|
| 5,569,256 A | 10/1996 | Vaughn et al. | |
| 5,620,447 A | 4/1997 | Smith et al. | |
| 5,624,214 A | 4/1997 | Carroll | |
| 5,624,447 A | 4/1997 | Myers | |
| 5,632,759 A | 5/1997 | Rexroth | |
| 5,649,930 A | 7/1997 | Kertzner | |
| 5,667,509 A | 9/1997 | Westin | |
| 5,685,673 A | 11/1997 | Jarvis | |
| 5,690,671 A | 11/1997 | McGurk | |
| 5,810,828 A | 9/1998 | Lightman et al. | |
| 5,908,423 A | 6/1999 | Kashuba et al. | |
| 5,913,867 A | 6/1999 | Dion | |
| 5,928,239 A * | 7/1999 | Mirza | 606/79 |
| 5,957,634 A | 9/1999 | Carpinetti | |
| 5,976,139 A | 11/1999 | Bramlet | |
| 5,997,582 A * | 12/1999 | Weiss | 606/89 |
| 6,024,749 A | 2/2000 | Shturman et al. | |
| 6,053,922 A | 4/2000 | Krause et al. | |
| 6,077,282 A | 6/2000 | Shturman | |
| 6,096,042 A | 8/2000 | Herbert et al. | |
| 6,110,211 A | 8/2000 | Weiss | |
| 6,156,069 A | 12/2000 | Amstutz | |
| 6,209,886 B1 | 4/2001 | Estes et al. | |
| 6,214,016 B1 | 4/2001 | Williams et al. | |
| 6,258,093 B1 * | 7/2001 | Edwards et al. | 606/80 |
| 6,358,251 B1 | 3/2002 | Mirza | |
| 6,517,519 B1 | 2/2003 | Rosen et al. | |
| 6,562,055 B2 | 5/2003 | Walen | |
| 6,607,530 B1 | 8/2003 | Carl et al. | |
| 6,656,195 B2 | 12/2003 | Peters et al. | |
| 6,716,215 B1 | 4/2004 | David et al. | |
| 6,726,223 B2 | 4/2004 | Haimer | |
| 6,740,090 B1 | 5/2004 | Cragg et al. | |
| 6,755,862 B2 | 6/2004 | Keynan | |
| 6,824,552 B2 | 11/2004 | Robison et al. | |
| 6,949,101 B2 | 9/2005 | McLeary et al. | |
| 7,682,378 B2 * | 3/2010 | Truckai et al. | 606/279 |
| 2001/0034526 A1 | 10/2001 | Kuslich | |
| 2002/0183758 A1 * | 12/2002 | Middleton et al. | 606/79 |
| 2002/0193799 A1 | 12/2002 | Veldman | |
| 2003/0078594 A1 | 4/2003 | Shturman et al. | |
| 2003/0191474 A1 * | 10/2003 | Cragg et al. | 606/79 |
| 2003/0191487 A1 | 10/2003 | Robison et al. | |
| 2003/0220641 A1 * | 11/2003 | Thelen et al. | 606/60 |
| 2004/0059317 A1 | 3/2004 | Hermann | |
| 2005/0113836 A1 | 5/2005 | Lozier | |
| 2006/0149268 A1 * | 7/2006 | Truckai et al. | 606/79 |

FOREIGN PATENT DOCUMENTS

| | | |
|---|---|---|
| EP | 0617927 A1 | 10/1994 |
| EP | 1149562 A2 | 10/2001 |
| EP | 1201191 A1 | 5/2002 |
| EP | 134834 A2 | 10/2003 |
| FR | 2802080 A1 | 6/2001 |
| JP | 11188043 A | 7/1999 |
| WO | WO02/051319 A2 | 7/2002 |

OTHER PUBLICATIONS

Election filed Aug. 11, 2008 in parent U.S. Appl. No. 11/095,232.

Office Action mailed Sep. 15, 2008 in parent U.S. Appl. No. 11/095,232.

* cited by examiner

ORTHOPAEDIC CUTTING INSTRUMENT AND METHOD

CROSS-REFERENCE TO RELATED APPLICATIONS

This application is a division of U.S. patent application Ser. No. 11/095,232, filed on Mar. 31, 2005, entitled "Orthopaedic Cutting Instrument and Method", the entire disclosure of which is expressly incorporated by reference herein.

FIELD OF THE INVENTION

The invention relates to orthopaedic cutting instruments used in orthopaedic surgery. In particular, the invention relates to powered instruments used to resect tissue.

BACKGROUND

Orthopaedic surgical procedures exist to treat a wide variety of conditions of the bones and joints of the human body. For example, procedures exist to remove damaged or diseased tissues such as bone tumors. Procedures also exist to replace damaged or diseased tissues such as joint replacement surgery in which the articular ends of the bones forming a joint are removed and replaced with prosthetic bearing components. During such procedures, tissue is removed from the surgical site using tissue cutting instruments such as saws, drills, shavers, and grinders. Many surgical procedures are now performed with surgical navigation systems in which sensors detect tracking elements attached in known relationship to an object in the surgical suite such as a surgical instrument, implant, or patient body part. The sensor information is fed to a computer that then triangulates the position of the tracking elements within the surgical navigation system coordinate system. Thus the computer can resolve the position and orientation of the object and display the position and orientation for surgeon guidance. For example, the position and orientation can be shown superimposed on an image of the patient's anatomy obtained via X-ray, CT scan, ultrasound, or other imaging technology.

SUMMARY

The present invention provides an orthopaedic cutting instrument and methods.

In one aspect of the invention, an orthopaedic cutting instrument includes a drive mechanism, a cutter coupled to the drive mechanism, means for driving the drive mechanism to produce oscillating rotary motion of the cutter; and means for adjusting the angular amplitude of the oscillating rotary motion.

In another aspect of the invention, an orthopaedic cutting instrument includes a handpiece including a motor, an elongated shaft extending from the handpiece and defining a shaft centerline, the shaft being coupled to the motor to transmit rotary motion from the motor, a cutter coupled to the shaft, and a control unit for driving the motor to produce oscillating rotary motion of the cutter about the shaft centerline.

In another aspect of the invention, an orthopaedic cutting instrument includes a drive mechanism, a cutter coupled to the drive mechanism, and means for driving the drive mechanism to preferentially cut relatively hard tissue and spare relatively soft tissue.

In another aspect of the invention, an orthopaedic cutting instrument includes a drive mechanism, a cutter coupled to the drive mechanism, means for tracking the cutter within a surgical navigation coordinate system, means for defining a cut zone within the surgical navigation coordinate system corresponding to a portion of the surgical site, means for driving the drive mechanism to cause the cutter to cut tissue when the cutter is within the cut zone, and means for stopping the drive mechanism to cause the cutter to cease cutting tissue when the cutter is outside of the cut zone.

In another aspect of the invention, a method of cutting tissue at a surgical site includes introducing a cutter into a surgical site; driving the cutter to preferentially cut relatively hard tissues as opposed to relatively soft tissues; and manipulating the cutter within the surgical site to morselize relatively hard tissues.

In another aspect of the invention, a method of cutting tissue at a surgical site includes introducing a cutter into a surgical site; tracking the position of the cutter with a surgical navigation system; and driving the cutter with cutter position dependent drive inputs.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

Embodiments of orthopaedic cutting instruments according to the present invention include a powered cutter for removing tissue at a surgical site. The surgical site may include such sites as a hip joint, knee joint, vertebral joint, vertebral body, shoulder joint, elbow joint, ankle joint, digital joint of the hand or foot, fracture site, tumor site, and/or other suitable surgical site. The instrument may include a powered handpiece containing a motor and a cutter head. The cutter head may be a separate modular cutter head engageable with the handpiece. The cutter head may include a circular blade, a convex burr, a grating shell, and/or other suitable cutter head configurations. The handpiece may drive the cutter head in oscillating motion and/or rotary motion. The cutter head motion may range from oscillation only to rotation only and combinations of oscillation and rotation. For example, the handpiece may drive the cutter head in a rotary motion mode to create an access portal in drill-like fashion and then be switched to an oscillating motion mode to selectively remove tissue at an accessed surgical site. An oscillating motion component may be controlled in amplitude and frequency so that the cutter head cutting action may be tailored to different tissues and to produce differing effects. For example, the oscillations of the cutter head may be configured to morselize relatively hard tissues while having no destructive effect on relatively soft tissues.

The handpiece may be driven pneumatically, hydraulically, electrically, or by other suitable means. For example, the handpiece may be driven by an electrical signal. The handpiece may be configured to turn in one direction with a first electrical polarity and in an opposite direction with the reverse polarity. Oscillatory motion may be achieved by inputting a step function that varies from positive to negative. Rotary motion may be achieved by supplying a constant voltage. Oscillatory and rotary motion may be combined by inputting an alternating step function overlaid with a constant direct current offset.

The entire instrument may be insertable into a surgical site or a portion of the instrument may remain outside of the surgical site while the cutter head is positioned within the surgical site. For example the handpiece may include an elongated barrel to facilitate accessing a surgical site. The barrel may be curved and/or may include a flexible portion to further facilitate accessing a surgical site. The barrel may be rotatable relative to the handpiece to position the barrel curve relative to the handpiece to facilitate reaching a particular surgical site. Furthermore, the barrel may be intraoperatively rotatable while the cutter head is positioned within the surgical site to cause the cutter head to sweep out an area larger than the cutter head. For example, an elongated barrel may be used to introduce the cutter head using a minimally invasive surgical approach through a small incision and along an access portal to a surgical site. For example, the cutter head may be introduced into a skeletal joint through a portal formed in a bone. The cutter head may then be driven to morselize bone adjacent the joint to prepare the joint to receive an implant. With the cutter head driven in oscillatory motion to preferentially morselize relatively hard tissues, the cutter head may be manually manipulated within the bone to remove the relatively harder bone without cutting the relatively softer cartilage and capsular tissues. Positioning of the cutter head may be further facilitated by use of fluoroscopic or other surgical imaging techniques.

A flexible portion may be steerable to guide the cutter head to a desired location and/or to sweep the cutter head back and forth to remove bone from a particular region. For example, a flexible portion may include embedded cables connected to an actuator such that moving the actuator steers the cutter head.

The instrument may include fluid delivery and/or fluid evacuation to expand soft tissue surrounding the surgical site to facilitate movement of the cutter head, to facilitate removal of resected tissue from the surgical site, and/or to cool the cutter head and tissue being cut. For example, the barrel may be cannulated and include a fluid delivery channel for delivering fluid to the surgical site. The fluid may include gases such as carbon dioxide and other suitable gases to insufflate the surgical site to provide more room to manipulate the cutter head. The fluid may include liquids such as saline and other suitable liquids to irrigate the surgical site to provide more room and/or to flush away resected tissues. The barrel may further include a fluid aspiration channel for allowing fluids to egress from the surgical site to facilitate controlling the pressure at the surgical site and also for removal of resected tissues. Fluid delivery and fluid evacuation channels may also be provided separately from the instrument such as with separate portals used in arthroscopy and endoscopy.

The instrument may include tracking elements detectable by a surgical navigation system such that the three dimensional position of the tracking elements can be related to a surgical navigation coordinate system. For example, a surgical navigation system may include multiple sensors at known locations that feed tracking element position information to a computer. The computer may then use the position information from the multiple sensors to triangulate the position of each tracking element within the surgical navigation coordinate system. The surgical navigation system can then determine the position and orientation of the cutter head by detecting the position and orientation of the tracking element and then resolving the position and orientation of the cutter head from the known relationship between the tracking array and the cutter head. Tracking elements may be detectable by imaging, acoustically, electromagnetically, and/or by other suitable detection means. Furthermore, tracking elements may be active or passive. Examples of active tracking elements may include light emitting diodes in an imaging system, ultrasonic emitters in an acoustic system, and electromagnetic field emitters in an electromagnetic system. Examples of passive tracking elements may include elements with reflective surfaces.

When used with a surgical navigation system, the instrument controller may be interfaced with the surgical navigation system to provide location dependent drive inputs to the handpiece. For example, a particular area within the surgical site may be identified within the surgical navigation system coordinate system as a cut zone and/or another area may be identified within the surgical navigation system coordinate system as a no-cut zone. Thus, with the surgical navigation system activated, the cutter head may be driven to resect tissue at the surgical site. If the cutting envelope of the cutter head begins to exit a cut zone and/or enter a no cut zone, a signal from the surgical navigation system to the instrument controller may cause the handpiece to stop the cutter head. Thus, the cutter head can be manually manipulated within the surgical site and the cutter head will only resect tissue when the cutting envelope of the cutter head is within a predefined area to be resected. The precise location of the cutter head may not be visible to the surgeon. However, the surgeon can manipulate the cutter head with confidence knowing that it will only be driven to resect tissue when it is in the predefined cut zone. Alternatively, the surgical navigation system may display a computer image showing the location of the cutter head relative to the patient's anatomy.

A steerable cutter head may be configured such that one or more actuators are motorized and coupled to a surgical navigation system. In such a system, the cutter head may be steered by the surgical navigation system to automatically manipulate the cutting envelope of the cutter head within a predefined cut zone to resect a particular region of the surgical site. Surgical navigated steering and surgical navigated cut/no-cut zones may be utilized together.

FIGS. 1-10 show an illustrative orthopaedic cutting instrument and its use in an illustrative surgical technique. The illustrative instrument includes a handpiece 100, modular cutter heads 200, 260, 280, and a control unit 300. The handpiece 100 includes a body 102 having a dependent grip 104, and a forwardly projecting barrel 106. The handpiece 100 houses a motor 108 coupled to a flexible drive shaft 110 extending from the motor 108, through the barrel 106, and terminating at a drive chuck 112. The drive chuck 112 receives the modular cutter heads 200, 260, 280 in torque transmitting relationship. The cutter heads 200, 260, 280 each include a cylindrical drive shaft 202, 262, 282 having a axial locking groove 204, 264, 284 and a "D"-shaped driving portion having a flat drive surface 206, 266, 286. The drive chuck has a complementary configuration including a "D"-shaped recess engageable with the driving portion and a ball detent for engaging the axial locking groove 204, 264, 284 to retain the cutter heads 200, 260, 280 as is known in the art. The motor 108 drives the drive shaft 110 in rotary motion which in turn drives the cutter heads 200, 260, 280 in rotary motion. In the illustrative instrument, the handpiece 100 defines a pistol grip with the body 102 defining a first axis 103 and the grip 104 defining a second axis 105 transverse to the body axis 103. The angle 107 between the two axes 103, 105 facilitates a comfortable grip while permitting natural pointing of the handpiece 100 and applying pressure to advance the handpiece 100 and cutter heads and move the cutter heads about within the surgical site. The angle 107 may be established to suit a particular surgical approach. However, an angle between 90° and 120° is generally suitable. Preferably the angle is approximately 110°.

Figures 1, 2:
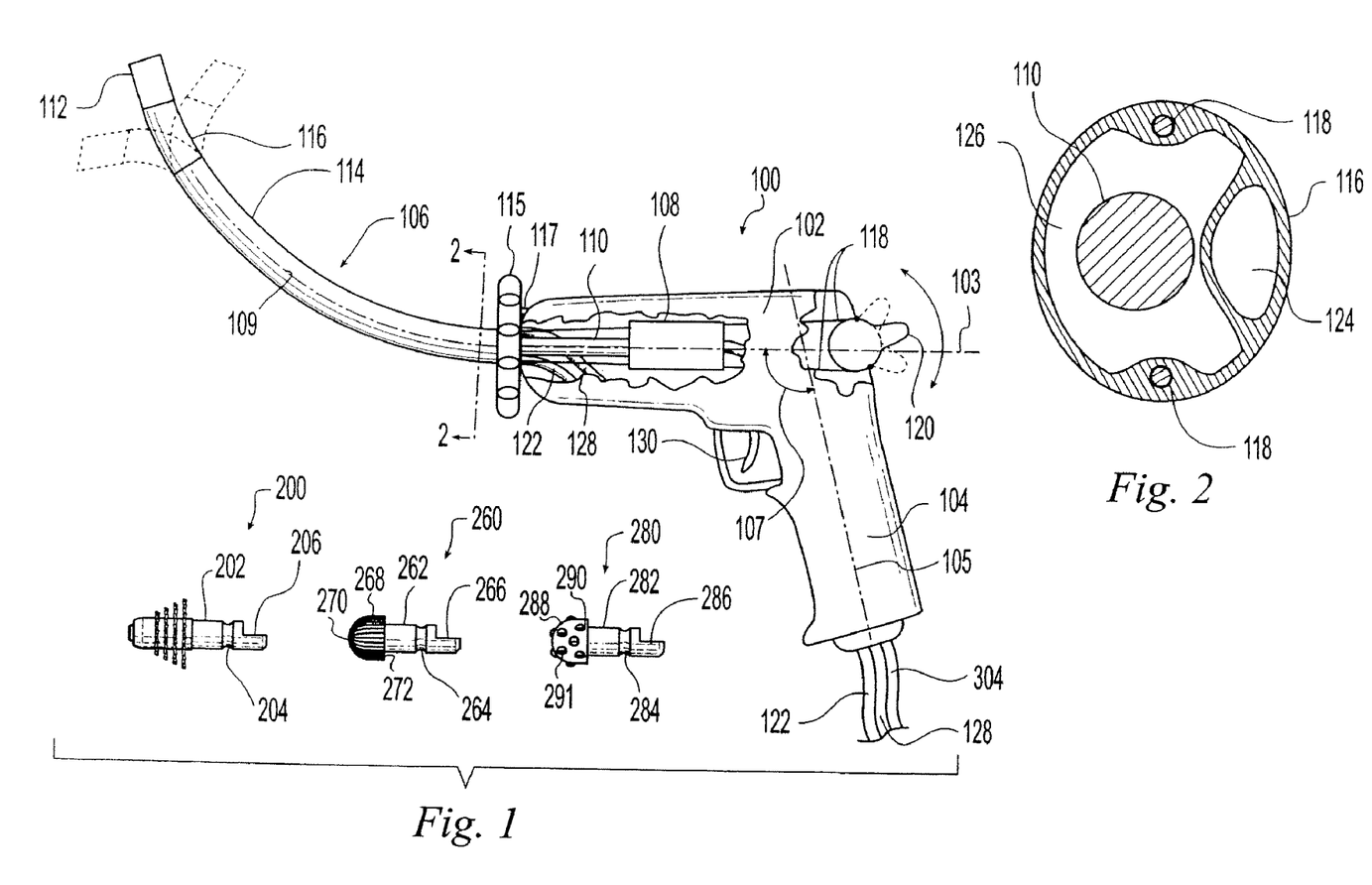
FIG. 1 is an exploded perspective view of an illustrative orthopaedic cutting instrument according to the present invention including a set of modular cutter heads.
FIG. 2 is a cross sectional view taken along line 2-2 of FIG. 1.

The illustrative handpiece 100 includes an elongated barrel 106 extending from the body 102 to facilitate access to surgical sites deep within a patient's body. The barrel 106 includes a centerline 109. The barrel 106 may be straight or curved. The illustrative barrel 106 includes a rigid curved portion 114 and a steerable portion 116. The curved portion 114 facilitates placing the cutter head in a surgical site that is not aligned with the body axis 103 when the handpiece is conveniently positioned. The barrel 106 is rotatable relative to the handpiece to position the curved portion 114 rotationally relative to the handpiece 100 to facilitate reaching a particular surgical site. An indexing wheel 115 is mounted on the barrel 106 and can be gripped and rotated to rotate the barrel 106. A ball detent 117 mounted in the body 102 engages the indexing wheel 115 to maintain the barrel 106 in a desired position. The cutter head may be moved within a surgical site to cut tissues by rocking the handpiece 100 back-and-forth and/or rotating the handpiece 100. The indexing wheel 115 may be used intraoperatively to rotate the barrel 106 and cause the cutter head to sweep out an area larger than the cutter head. The steerable portion 116 includes a flexible material such as an elastomer, a coil spring, and/or other suitable flexible materials that allow the steerable portion 116 to bend elastically. A pair of cables 118 attach to the steerable portion 116 and to an actuator 120 mounted in the handpiece 100. Pivoting the actuator 120 causes one of the cables 118 to pull on the steerable portion 116 and bend the steerable portion 116 causing the drive chuck 112 and attached cutter head to change orientation. The steerable portion 116 permits changing the angle of the cutter head relative to the barrel centerline 109 to achieve greater movement or the cutter head within the surgical site. The illustrative handpiece 100 has a pair of cables 118 permitting control of the steerable portion 116 in one plane. However, it is contemplated that any number of cables and/or other linkages may be used to permit control of the steerable portion 116 in any number of planes. For example, four cables 118 may be used with two actuators 120 to bend the steerable portion 116 in three dimensions. The illustrative actuator 120 is shown as a manually operated thumb lever projecting from the body 102. However, it is contemplated that the actuator 120 may be powered, such as by a motor.

The illustrative barrel is cannulated to provide fluid delivery and aspiration to and from the surgical site. Fluid is transmitted from a fluid reservoir (not shown) through supply line 122, through fluid delivery portal 124 and out the drive chuck 112. Fluid and debris are transmitted from the surgical site through the drive chuck 112, through aspiration portal 126 and out suction line 128. The cutter heads 200, 260, 280 may optionally be cannulated so that fluid delivery and aspiration occur through the cutter heads.

Figures 3, 4:
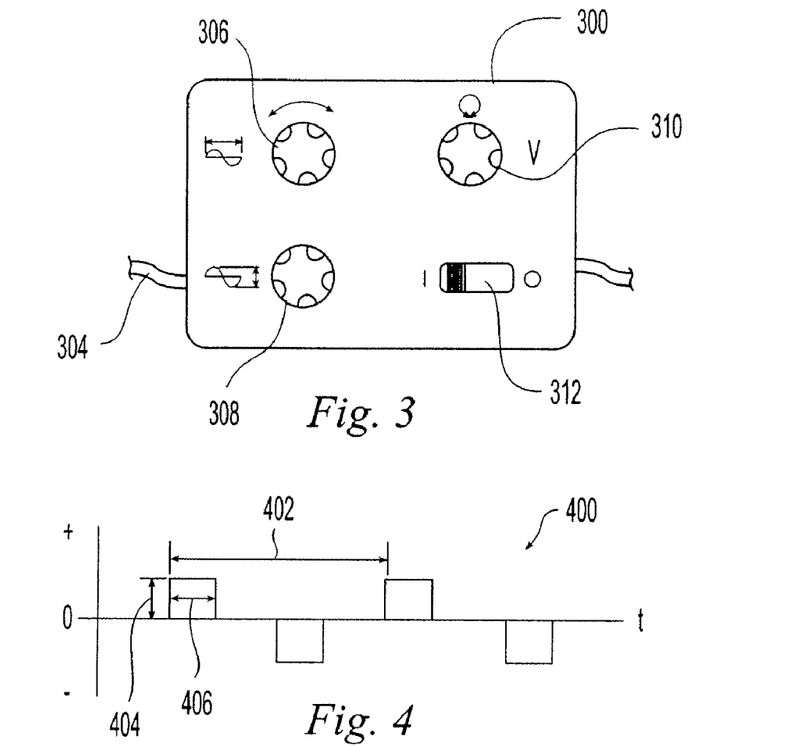
FIG. 3 is a front elevation view of a controller for the orthopaedic cutting instrument of FIG. 1.
FIG. 4 is a diagram showing a drive input for producing oscillating cutter head motion.

The handpiece further includes a trigger 130 coupled to the motor 108 to permit operator control of the motor 108. The control signal for the motor 108 is provided by a control unit 300 which may be part of the handpiece 100 or a separate unit as shown in FIG. 3. The control unit 300 includes a power input 302 and a power output 304. The power output 304 connects to the handpiece 100 and drives the motor 108. The power input 302 and output 304 may be pneumatic, hydraulic, and/or electric. In the illustrative example, the power is electric. The trigger 130 interrupts the power connection from the power output 304 to the motor 108 in the rest position such that activating the trigger permits the motor 108 to operate. Optionally, the trigger can be configured to vary the amplitude of the control signal from zero when the trigger 130 is at rest to the maximum output control signal when the trigger 130 is fully depressed.

Figure 5:
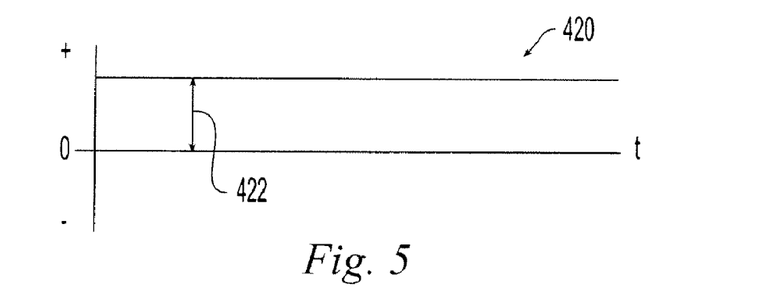
FIG. 5 is a diagram showing a drive input for producing rotating cutter head motion.
Figure 6:
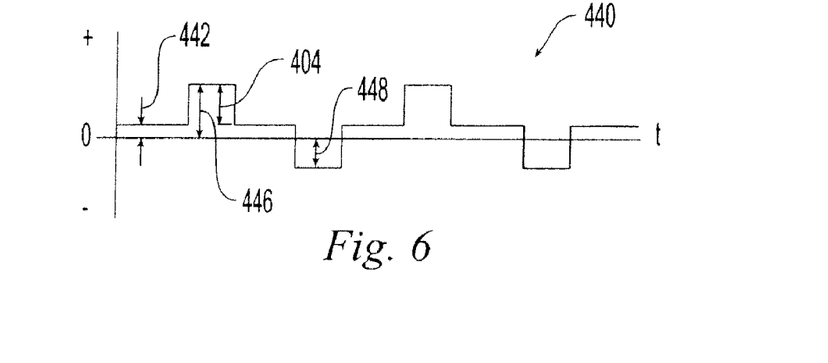
FIG. 6 is a diagram showing a drive input for producing combined oscillating and rotating cutter head motion.

The control unit 300 includes controls for adjusting the power output 304 to produce a desired cutter head action. FIGS. 4-6 depict resulting illustrative power output 304 signals 400, 420, 440 for driving the motor 108. The illustrative signals are characterized by step functions having positive values (positive polarity in an electrical system, positive pressure in pneumatic and hydraulic systems) that cause the motor 108 to rotate clockwise and negative values (negative polarity in an electrical system, negative pressure in pneumatic and hydraulic systems) that cause the motor to rotate counterclockwise. Referring to the signal depicted in FIG. 4, the time for the signal to cycle from the start of one positive step to the start of the next positive step is the period 402 of the signal. The inverse of the period 402 is the frequency. The height 404 of each step determines the rotational speed of the motor and the length of each step 406 determines how long the motor 108 is driven in each direction. The height 404 and length 406 together determine how far the motor 108 rotates in each direction and thus controls the angular amplitude of the motor and cutter head. Increasing either of the height 404 and length 406 will increase the angular amplitude and decreasing either of the height 404 and length 406 will decrease the angular amplitude. In the illustrative signals, the length 406 of the steps is kept constant and the height 404 is adjustable. Referring to FIG. 5, a constant positive signal 420 is illustrated which will cause the motor 108 to rotate constantly clockwise. The height 422 of the signal will determine the rate of rotation. FIG. 6 illustrates a signal 440 combining the oscillating characteristics of FIG. 4 with a constant positive offset 442 like that of FIG. 5. The effect of this combined signal 440 is that the motor 108 will oscillate while rotating clockwise.

The control unit 300 of FIG. 3 includes a period control knob 306 that is rotated to adjust the period 402 of the motor oscillations, an amplitude control knob 308 that is rotated to adjust the height 404 of the step function and thus the amplitude of angular oscillation, and a rotation control knob 310 that introduces a constant offset. Rotating the rotation control knob 310 clockwise increases the offset in the positive direction. Rotating the rotation control knob 310 counterclockwise increases the offset in the negative direction. A power switch 312 turns the control unit on an off. An infinite variety of control signals can be produced by adjusting the control knobs 306, 308, 310. For example, setting the oscillation control knobs 306 and 308 to zero and adjusting the rotation control knob 310 clockwise will provide a constant positive drive signal upon trigger 130 activation to turn the cutter head. In this mode, the handpiece will act like a drill. The rotational speeds can advantageously range from 0-100,000 rpm or more. Larger cutting heads are advantageously driven at slower speeds while smaller cutter heads are advantageously driven at faster speeds. For example a large cutter head or drill bit may be driven between 100 and 1000 rpm to create an access portal through a bone. In another example, setting the rotation control 310 to zero and adjusting the oscillating controls 306 and 308 to non-zero values will cause the handpiece 100 to oscillate the cutter head. The oscillation angle can range from 0° to any value. Advantageously the oscillation angle is between 0° and 180°. Having all three controls 306, 308, 310 set to non-zero values will cause the handpiece 100 to oscillate and rotate the cutter head simultaneously.

As long as the offset 442 of FIG. 6 is less than the relative height 444 of the steps, the motor will oscillate in both directions as it rotates. However, in the example of FIG. 6, the motor will rotate clockwise at a faster rate, and thus further angularly, than it will counterclockwise because the net positive signal height 446 resulting from adding in the offset 442 is greater than the net negative signal height 448. If the offset 442 equals or exceeds the relative height 444 of the steps, the motor will not actually oscillate but will pulse in one direction as it turns.

Different tissues respond differently to different cutter head motions and blade configurations. For example, different tissues can tolerate different amounts of lineal displacement before they begin to tear, fracture, or otherwise become disrupted. The amount of lineal displacement of a cutter head tooth and consequently the amount of lineal displacement to which tissue abutting the tooth is subjected is a function of the angular motion of the cutter head and the radius from the rotational axis to the tooth. The control unit 300 may include markings and/or preset switches corresponding to predetermined values indicating optimum control settings for different types of cutter heads and different tissues. For examples there may be a predetermined optimum setting for a circular blade style cutter head 200 and cortical bone and another optimum setting for a grater style cutter head 280 and cartilage.

Figure 7:
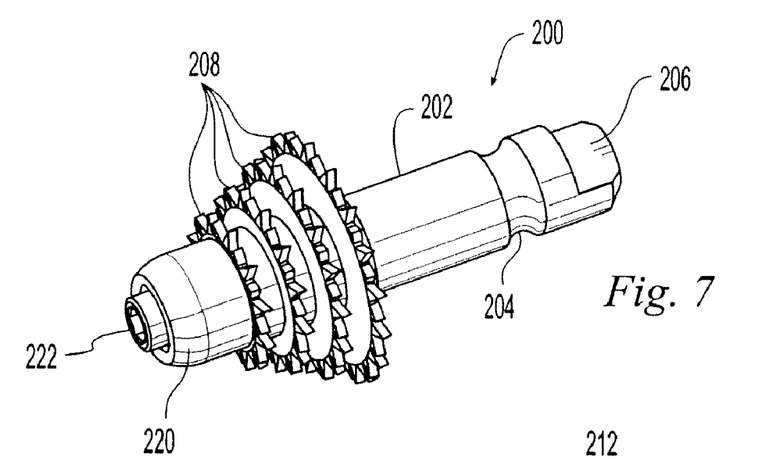
FIG. 7 is a perspective view of one of the cutter heads of FIG. 1.
Figure 8:
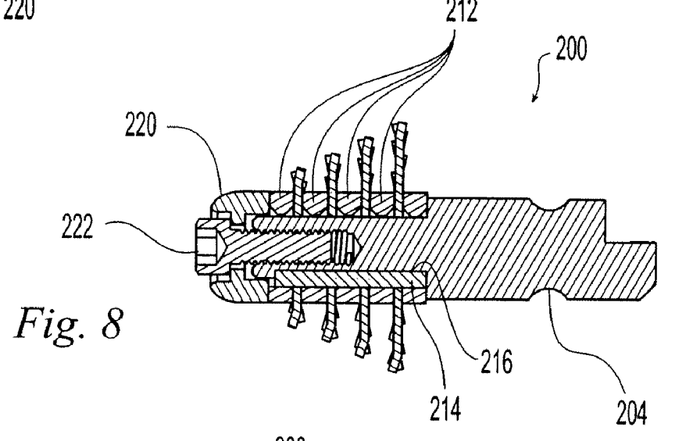
FIG. 8 is a cross sectional view of the cutter head of FIG. 7.
Figure 9:
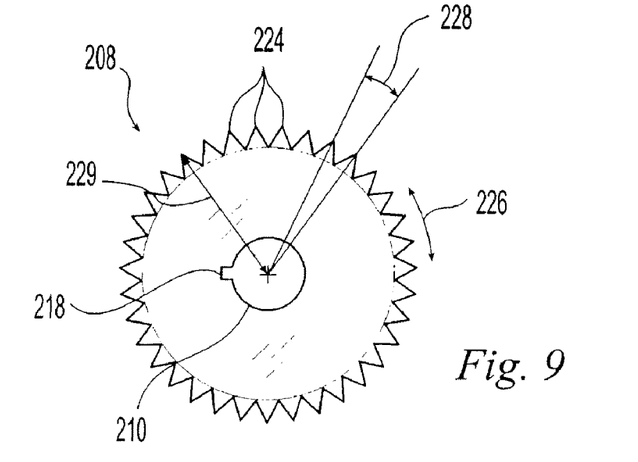
FIG. 9 is a side elevation view of a blade of the cutter head of FIG. 7.

FIGS. 7-9 illustrate the circular blade style cutter head 200 of FIG. 1 in more detail. The cutter head 200 includes a cylindrical drive shaft 202 having an axial locking groove 204 and a "D"-shaped driving portion having a flat drive surface 206 as is known in the art. The cutter head 200 further includes a plurality of blades 208 spaced along the shaft 202. Each blade 208 includes a central bore 210 that slips over the shaft 202. Spacers 212 fit between the blades 208 to space them from one another. A key 214 fits within a keyway 216 in the shaft 202 and engages a notch 218 in each blade to rotationally lock the blades 208 to the shaft 202. An end cap 220 presses the spacers and blades together axially and is secured with a bolt 222 threaded into the shaft 202. The end cap 220 defines a blunt nose on the cutter head. The blades 208 include a plurality of teeth 224 spaced around their perimeters. Preferably, the teeth 224 are set in an alternating pattern to provide for chip clearance and more efficient cutting. In the illustrative example, the blades 208 have graduated diameters increasing from a relatively small diameter blade near the end cap 220 to a relatively large diameter blade spaced from the end cap 220. The graduated blades 208 define a frustoconical cutting envelope. However, it is contemplated that the blades 208 may vary in diameter in other patterns or may all be the same diameter. The modular nature of the illustrative example permits the blade configuration to be easily changed by the user.

When the cutter head 200 is used in an oscillating mode the blades 208 tend to cut relatively hard tissues, such as bone, aggressively while relatively soft tissues such as meniscal cartilage and capsular ligaments are not cut. It is believed that since hard tissues are less mobile local to the teeth 224, the oscillating motion of the blades 208 fractures the bone and thereby morselizes it. Conversely, relatively soft tissues are more mobile local to the teeth 224 and tend to move back and forth with the teeth 224 without being cut. As long as the lineal displacement of the teeth 224 is within the range of displacement that the soft tissue can tolerate without being cut, oscillating the cutter head 200 in an environment including both soft and hard tissues will tend to morselize the hard tissue while leaving the soft tissue intact. The lineal displacement of a tooth 224 is equal to twice the product of the radius 229 from the rotational axis to the tooth tip and the oscillation amplitude 226 in radians. Furthermore, during oscillation, soft tissues do not wrap around the blade or otherwise entangle it. The present investigators have found that when the oscillating amplitude 226 exceeds the tooth angular spacing 228, the blades 208 cut much more aggressively in hard tissues such as bone. Likewise, when the oscillating amplitude 226 is less than the tooth angular spacing 228, the blades cut much less aggressively. For example, it has been found that with the illustrative blade shown in FIGS. 7-9, a blade radius 229 of 0.3 inches with a tooth spacing of 8° and an oscillation amplitude of 10° produces good cutting results in bone while not cutting adjacent soft tissues.

An optional cutter head 260 is also depicted in FIG. 1. This cutter head 260 includes circumferentially spaced longitudinal teeth 268 extending along the other surface of the cutter head 260 from the cutter head pole 270 to its equator 272. This cutter head 260 is end cutting and can be used to penetrate tissue and form an access portal. It can also be configured as a collapsible cutter head to permit it to fit through a small, preformed access portal and then be expanded at the surgical site. For example, the cutter head 260 may be formed from a flexible material with cutting teeth 268 attached to its outer surface. In the collapsed state, the teeth 268 are closely spaced and the cutter head 260 occupies a first volume. When it is expanded, the cutter head 260 occupies a second, larger volume and the teeth 268 are more widely spaced. The cutter head 260 may be formed of an elastic or inelastic flexible material such as an elastomer, fabric, film, foil, and/or other suitable material. The teeth may be formed of metal, polymer, ceramic, and/or other suitable material. For example, an elastomeric cutter head 260 may be in the form a hollow molded synthetic rubber cylinder with metal teeth 268 embedded in its outer surface. The cutter head 260 may be inserted through a relatively small access portal and then expanded by inflating it with air, saline, and/or other suitable fluid into its hemispherical cutting shape. After the cutter head 260 has been used, it may be deflated and withdrawn. Alternatively, an inflatable core can be covered with a woven mesh similar to chain mail to provide an abrading and/or cutting surface. Likewise, an expandable cutter head may include a mechanical arrangement of hinged blades and or other mechanism that permits the cutting diameter to be varied.

Another optional cutter head 280 is also depicted in FIG. 1. This cutter head 280 includes a hollow shell 288 having an outer surface and an inner surface. Grater style teeth 290 project outwardly from the outer surface of the shell 288. The shell 288 includes openings 291 communicating from the outer surface to the inner surface to allow tissue cut by the teeth 290 to pass to the inside of the head where it can be easily aspirated or where it can be retained for subsequent removal. This cutter head 280 facilitates the collection of tissue for purposes of tissue grafting, laboratory assay, and/or other purposes. The illustrative grater style cutter head 280 has teeth that all face in the same rotational direction such that it cuts in one direction only. To cut tissue, the cutter head 280 may be oscillated, pulsed, or rotated. When driven in reverse rotary mode, the cutter head 280 will not cut tissue but can be used to smooth and consolidate tissues.

Figures 10, 11:
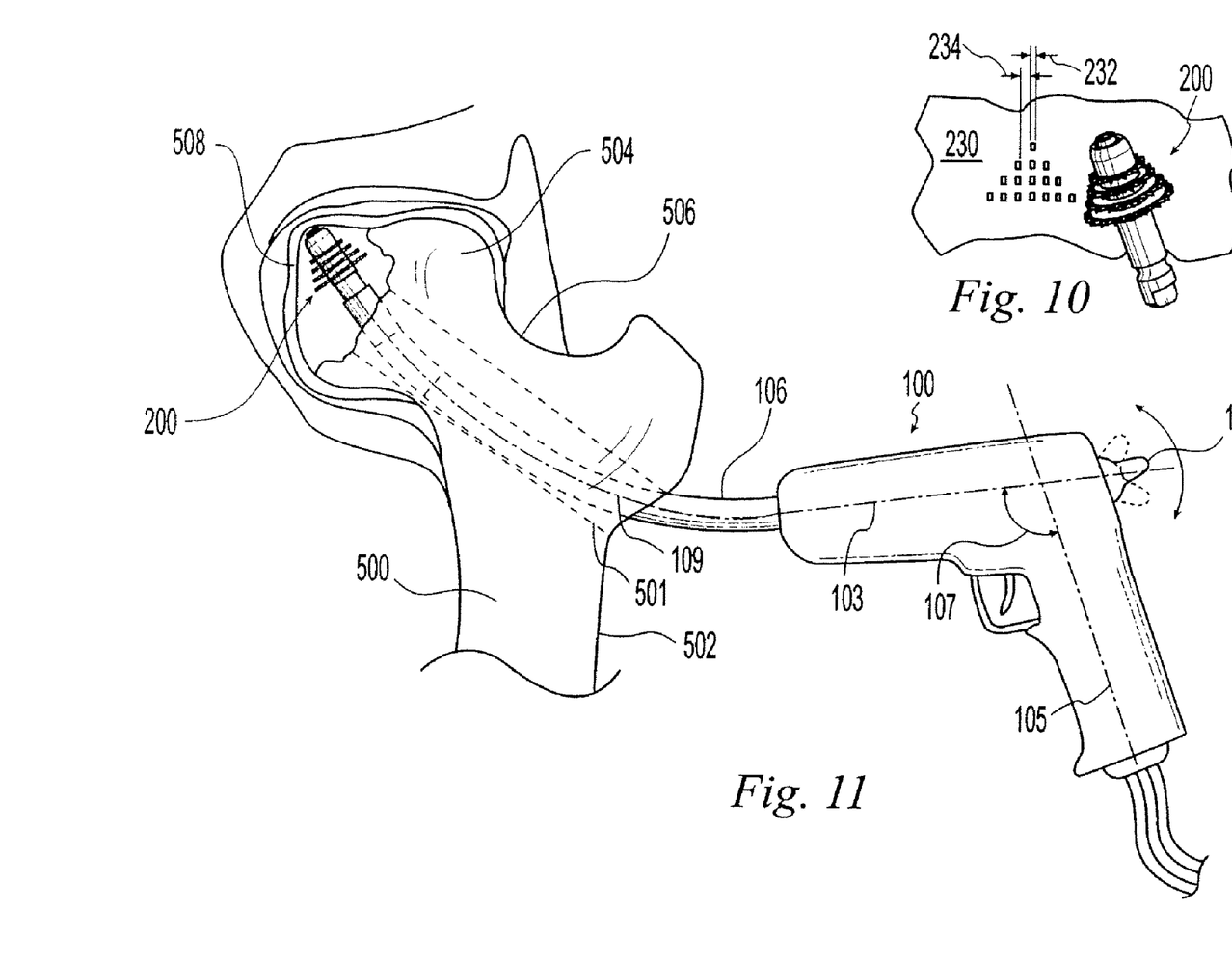
FIG. 10 is perspective view of tissue cut by the cutter head of FIG. 7.
FIG. 11 is a side elevation view of the instrument of FIG. 1 in use to prepare a femoral bone to receive an implant.

FIG. 10 illustrates the effects of varying the relationship of the tooth angular spacing 228 and the oscillation amplitude 226. As the cutter head 200 is oscillated against a relatively hard tissue 230 such as bone, the teeth 224 will cut into the tissue 230. If the oscillation amplitude 226 is less than the tooth angular spacing 228, the teeth will cut grooves 232 in the tissue separated by uncut areas 234. This may be desirable, for example, to score a bone to produce bleeding bone to stimulate bone growth or to roughen a bone to accept bone cement. As the oscillation amplitude 226 is increased relative to the tooth spacing 228, the grooves 232 will widen and the uncut areas 234 will become more narrow until the oscillation amplitude 226 is equal to or greater than the tooth spacing 228 in which case the tooth will remove all of the bone between adjacent teeth 224. Thus, for efficient tissue removal, it is advantageous for the oscillation amplitude 226 to exceed the tooth spacing 228. However, in some instances it may be advantageous to have relatively widely spaced teeth and relatively small oscillation amplitude 226. For example, with the grater style cutter head 280, it may be difficult to produce a cutter head with closely spaced teeth. In another example, it may be desirable to have widely spaced teeth in order to cut the tissue into larger pieces. Furthermore, it may be more efficient to drive the cutter head with high frequency and low amplitude oscillations. In any situation where the tooth spacing 228 is greater than the oscillation amplitude 226, complete removal of tissue between adjacent teeth 224 may be accomplished by rotating the cutter head in addition to oscillating it to cause the teeth to progress across the surface of the tissue. A relatively slow rotation velocity is sufficient.

In use, the instrument may be used to excise bone by inserting it into a surgical site and relying on the preferential cutting characteristics of a particular cutter head and operation mode to remove the desired tissue. For example, in a hip joint application as shown in FIG. 11, the cutter head 200 is introduced through a portal 501 defining a longitudinal portal axis in the lateral side 502 of the femur 500. The portal 501 can be pre-drilled with a conventional drill bit or it can be produced with the present instrument by using an end cutting cutter head, such as the cutter head 260 (FIG. 1) and running the handpiece 100 in rotating mode. The cutter head 200 is advanced to the surgical site and then oscillated to morselize the femoral head 504 and neck 506. However, soft tissues 508, such as the joint cartilage and capsular ligaments, are not cut by the oscillating cutter head 200 and thus contain the cutting action to the bone of the head 504 and neck 506. The cutter head 200 is manipulated within the surgical site by rocking the handpiece 100 and barrel 106 back-and-forth to move the cutter head 200 off of the portal axis 503. Rotating the handpiece 100 about the body axis 103 causes the cutter head 200 to sweep out an area larger than the cutter head 200 around the portal axis 503. To further aid in reaching the entire surgical site, the cutter head 200 can be steered using the actuator 120 to change the angle of the cutter head to the barrel centerline 109. Morselized bone is mobilized and removed by irrigating and aspirating the surgical site with saline introduced and removed through the cannulated barrel 106. The instrument may be used blindly relying on its preferential cutting ability. Alternatively, a visualization system may be used to monitor the progress of the cutter head 200. For example, a fluoroscopic imaging system may be used to visually track the cutter head 200.

Optionally, the cutter head may include a tracking element trackable by a surgical navigation system. For example, the end cap 220 may include a tracking element in the form of an electromagnetic coil. By detecting the position of the coil, the surgical navigation system can resolve the location of the cutting envelope defined by the moving blades 208. The position of the cutting envelope may be combined with other patient data such as that from x-rays, MRI scans, CT scans, and/or other sources and displayed for surgeon guidance. Furthermore, the control unit 300 may be interfaced with the surgical navigation system to provide location dependent drive inputs to the handpiece 100. For example, a particular area within the surgical site such as the femoral head 504 and neck 506 may be identified within the surgical navigation system coordinate system as a cut zone and another area, such as the acetabulum and/or joint capsule, may be identified within the surgical navigation system coordinate system as a no-cut zone. Thus, with the surgical navigation system activated, the cutter head 200 may be driven to resect tissue at the surgical site. If the cutting envelope of the cutter head 200 begins to exit a cut zone and/or enter a no-cut zone, a signal from the surgical navigation system to the instrument controller 300 will cause the handpiece to stop the cutter head 200. Thus, the cutter head 200 can be manually manipulated within the surgical site and the cutter head 200 will only resect tissue when the cutting envelope of the cutter head 200 is within a predefined area to be resected. The precise location of the cutter head 200 may not be visible to the surgeon. However, the surgeon can manipulate the cutter head 200 with confidence knowing that it will only be driven to resect tissue when it is in the predefined cut zone. This navigated control option also permits the use of more aggressive cutter heads and operation modes while protecting tissues in the no-cut zones. The cutter head may be driven in any mode including rotating, oscillating, and mixed rotating and oscillating mode. However, driving the cutter head in an oscillating mode advantageously permits rapid stopping of the cutter head since it may develop less angular momentum and the cutter head is already being frequently stopped and reversed to produce the oscillating motion. The surgical navigation system can also be configured to indicate portions of the cut zone that the cutting envelope has not yet passed through so that the cutter head 200 can be repositioned in these uncut areas until all of the desired tissue has been cut.

A steerable configuration may include one or more motorized actuators 120 coupled to the surgical navigation system. In such a system, the cutter head 200 may be steered by the surgical navigation system to automatically manipulate the cutting envelope of the cutter head within the predefined cut zone to efficiently resect the cut zone.

The cutter head 200 may have tracking elements attached at other locations. Furthermore, tracking elements may be attached outside of the surgical site as long as the relationship of the tracking elements to the cutter head 200 is known. For example, where the relationship of the cutter head 200 to the barrel 106 or handpiece 100 is known, the tracking elements may be attached to the barrel 106 or handpiece 100. Any type of tracking element may be used.

Although examples of an orthopaedic cutting instrument and its use have been described and illustrated in detail, it is to be understood that the same is intended by way of illustration and example only and is not to be taken by way of limitation. The invention has been illustrated in the context of a handpiece, controller, and modular cutter head and has been shown in use to resect a femoral head and neck in a minimally invasive procedure. However, the orthopaedic cutting instrument may be alternatively configured and may be used to remove other types of tissue at other locations within a patient's body. Accordingly, variations in and modifications to the orthopaedic cutting instrument and its use will be apparent to those of ordinary skill in the art, and the following claims are intended to cover all such modifications and equivalents.

What is claimed is:

1. A method of cutting tissue at a surgical site comprising:
   introducing a cutter into a surgical site having relatively hard tissues and relatively soft tissues, the cutter including a blade having a blade tip rotatable about a rotational axis, the blade tip spaced from the rotational axis by a radius;
   driving the blade tip of the cutter through a rotational amplitude, such that a lineal displacement of the blade tip is equal to twice the product of the radius and the rotational amplitude, the lineal displacement less than a displacement that the relatively soft tissues can tolerate without being cut but more than the relatively hard tissues can tolerate without being cut, whereby the cutter is adapted to cut the relatively hard tissues without cutting the relatively soft tissues; and
   manipulating the cutter within the surgical site to morselize relatively hard tissues.

2. The method of claim 1, wherein the cutter extends from a barrel having a barrel centerline, at least a portion of the barrel centerline coincident with the rotational axis of the blade tip.

3. The method of claim 1, wherein the cutter includes a plurality of blades, each of the blades having a respective blade tip, adjacent ones of the blade tips defining a blade tip spacing therebetween, the blade tip spacing less than the lineal displacement of the blade tip.

4. The method of claim 1, wherein the cutter includes a plurality of blades, each of the blades having a respective blade tip, adjacent ones of the blades defining an angular blade spacing therebetween, the angular blade spacing less than the rotational amplitude.

5. The method of claim 4, wherein the angular blade spacing is about 8 degrees.

6. The method of claim 1, wherein the rotational amplitude is less than 360 degrees.

7. The method of claim 6, wherein the rotational amplitude is about 10 degrees.

8. The method of claim 1 wherein the cutter is mounted on a curved shaft and further wherein manipulating the cutter comprises moving the shaft from side to side and rotating the shaft to cause the cutter to sweep an area larger than the cutter diameter.

9. The method of claim 1 wherein the cutter is mounted on an elongated shaft and the shaft includes a steerable portion, manipulating the cutter comprising steering the steerable portion to cause the cutter to change position relative to the shaft.

10. The method of claim 1 wherein driving the blade tip of the cutter comprises moving the cutter in an oscillating rotary motion.

11. The method of claim 10 further comprising:
    adjusting the rotational amplitude to adjust the cutting characteristics of the cutter.

12. The method of claim 10 further comprising:
    adjusting an oscillation frequency to adjust the cutting characteristics of the cutter.

13. The method of claim 1 wherein introducing a cutter into a surgical site comprises moving the cutter in a continuous rotary motion to form an access portal and driving the blade tip of the cutter comprises moving the cutter in an oscillating rotary motion.

14. The method of claim 1 wherein introducing a cutter into a surgical site comprises forming a portal through a femur from the lateral side of the femur to the hip joint.

15. The method of claim 14 wherein driving the cutter selectively removes the femoral head.

* * * * *